United States Patent [19]

Lepone

[11] Patent Number: 4,740,234

[45] Date of Patent: Apr. 26, 1988

[54] HERBICIDAL ORTHO-CARBOMETHOXYSULFONYLUREAS

[75] Inventor: Gerald E. Lepone, Elkton, Md.

[73] Assignee: E. I. DuPont De Nemours and Company, Wilmington, Del.

[21] Appl. No.: 42,269

[22] Filed: Apr. 24, 1987

Related U.S. Application Data

[63] Continuation of Ser. No. 732,783, May 10, 1985, abandoned.

[51] Int. Cl.$^4$ .................. C07D 251/16; C07D 251/42; A01N 43/66
[52] U.S. Cl. ........................................ 71/93; 544/211
[58] Field of Search ............................. 71/93; 544/211

[56] References Cited

U.S. PATENT DOCUMENTS 4,383,113  5/1983  Levitt ................................. 544/211

Primary Examiner—John M. Ford

[57] ABSTRACT

A designated o-carbomethoxysulfonylurea demonstrates high activity as a herbicide.

8 Claims, No Drawings

HERBICIDAL ORTHO-CARBOMETHOXYSULFONYLUREAS

This is a continuation of application Ser. No. 732,783, filed 5-10-85, now abandoned.

BACKGROUND OF THE INVENTION

A designated o-carbomethoxysulfonylurea is an extremely attractive agricultural chemical. It has high herbicidal activity and low residual activity.

The compound of the instant invention is generically disclosed in U.S. Pat. No. 4,383,113.

There is a continual need for herbicides which have high activity, selectivity for important crops such as cereals, and low residual activity.

The importance of cereal crops for feeding mankind is well-known. Unfortunately, some of the known herbicides have high residual activity. Thus, crops cannot easily be rotated in an area in which the herbicide is present.

Thus, there is a need for herbicides with high activity as herbicides but low residual activity to facilitate rotation of crops.

SUMMARY OF THE INVENTION

According to the instant invention, such a compound has been discovered.

This invention pertains to the compound of Formula I, its agriculturally suitable compositions and its method-of-use as a selective postemergent herbicide, particularly for cereal crops (wheat and barley).

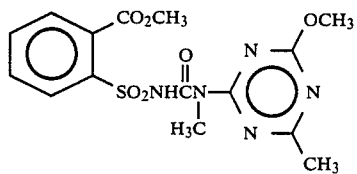

The compound is 2-[[N-(4-methoxy-6-methyl-1,3,5-triazin-2-yl)-N-methylaminocarbonyl]aminosulfonyl]-benzoic acid, methyl ester, m.p. 146°-148° C. The compound also undergoes rapid soil dissipation and would ordinarily possess no recrop limitations.

DETAILED DESCRIPTION OF THE INVENTION

As part of the present invention, it has been found that unexpectedly high herbicidal activity with safety to wheat and barley, is exhibited by 2-[[N-(4-methoxy-6-methyl-1,3,5-triazin-2-yl)-N-methylaminocarbonyl]aminosulfonyl]benzoic acid, methyl ester. The compound of the present invention has the Formula I.

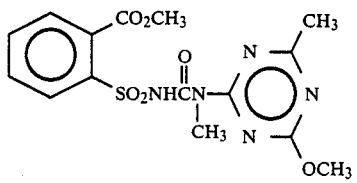

Synthesis

The title compound of Formula I can be prepared by the reaction of 2-carbomethoxybenzenesulfonyl isocyanate (II) with 2-methoxy-4-methyl-6-methylamino-1,3,5-triazine (III). The reaction is best carried out in an inert aprotic organic solvent such as dichloromethane, 1,2-dichloroethane, tetrahydrofuran or acetonitrile at a temperature between 20° and 85° C.

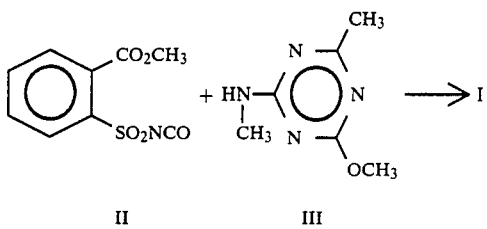

The preparation of the intermediate sulfonyl isocyanate II is disclosed in U.S. Pat. No. 4,394,506. The preparation of the aminotriazine III is taught by T. Tsujikawa et al. in *Yakugaku Zasshi*, 95, 512 (1975) or in Japanese Patent Application 2177('66) (Chem. Abs., 64, 14200 g, 1966).

The following example further illustrates the present invention.

EXAMPLE 1

2-[[-N-[4-methoxy-6-methyl-1,3,5-triazin-2-yl]N-methylaminocarbonyl]aminosulfonyl]benzoic acid, methyl ester To a solution of 2-carbomethoxybenzenesulfonyl isocyanate (22.4 g 93.0 mmol) in dichloromethane (100 mL) was added 2-methoxy-4-methyl-6-methylamino-1,3,5-triazine (10.7 g, 69.6 mmol), followed by a catalytic amount of 1,4-diaza[2.2.2]bicyclooctane. After stirring overnight at ambient temperature under a nitrogen atmosphere, the reaction mixture was concentrated in vacuo. The residue was triturated with diethyl ether and then washed with 1-chlorobutane to yield the title compound as a white powder (27.8 g, m.p. 126°–131° C.).

IR(KBr): 1735 (C=O), 1720 (C=O), 1570, 1470, 1430, 1350 ($SO_2$), 1285, 1270, 1170 ($SO_2$) and 1160 $cm^{-1}$.

NMR ($CDCl_3$/DMSO) δ 2.7 (s, HET-$CH_3$) 3.4 (s, N-$CH_3$) 3.9 (s, $CO_2CH_3$) 4.05 (s, HET-$OCH_3$) 7.35–7.75 (m, ArH) 8.15–8.4 (m, ArH) 14.0 (broad, NH).

A modification of this procedure involving reduction of the reaction volume, followed by the addition of xylene, led to precipitation of the title compound as a white powder, m.p. 146°–148° C.

Formulations

Useful formulations of the compound of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE I

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of addi-tives to reduce foaming, caking, corrosion, microbio-logical growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:
- H. M. Loux, U.S. Pat. No. 3,235,361, Feb. 15, 1966, Col. 6, line 16 through Col. 7, line 19 and Examples 10 through 41;
- R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;
- H. Gysin and E. Knusli, U.S. Pat. No. 2,891,855, June 23, 1959, Col. 3, line 66 through Col. 5, line 17 and Examples 1-4;
- G. C. Klingman, "Weed Control as a Science", John Wiley and Sons, Inc., New York, 1961, pp. 81-96; and
- J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 2

Wettable Powder

| | |
|---|---|
| 2-[[N—(4-methoxy-6-methyl-1,3,5-triazin-2-yl)-N—methylaminocarbonyl]aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

Wettable Powder

| | |
|---|---|
| 2-[[N—(4-methoxy-6-methyl-1,3,5-triazin-2-yl)-N—methylaminocarbonyl]aminosulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

Granule

| | |
|---|---|
| Wettable Powder of Example 3 | 5% |
| attapulgite granules (U.S.S. 20-40 mesh; 0.84-0.42 mm) | 95% |

A slurry of wettable powder containing 25% solids is sprayed on the surface of attapulgite granules while tumbling in a double-cone blender. The granules are dried and packaged.

EXAMPLE 5

Extruded Pellet

| | |
|---|---|
| 2-[[N—(4-methoxy-6-methyl-1,3,5-triazin-2-yl)-N—methylaminocarbonyl]aminosulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Oil Suspension

| | |
|---|---|
| 2-[[N—(4-methoxy-6-methyl-1,3,5-triazin-2-yl)-N—methylaminocarbonyl]aminosulfonyl]benzoic acid, methyl ester | 25% |
| polyoxethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 7

Wettable Powder

| | |
|---|---|
| 2-[[N—(4-methoxy-6-methyl-1,3,5-triazin-2-yl)-N—methylaminocarbonyl]aminosulfonyl]benzoic acid, methyl ester | 20% |
| sodium alkynaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 8

Low Strength Granule

| | |
|---|---|
| 2-[[N—(4-methoxy-6-methyl-1,3,5-triazin-2-yl)-N—methylaminocarbonyl]aminosulfonyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

Aqueous Suspension

| | |
|---|---|
| 2-[[N—(4-methoxy-6-methyl-1,3,5-triazin-2-yl)-N—methylaminocarbonyl]aminosulfonyl]benzoic acid methyl ester | 40.0% |
| polyacrylic acid thickener | 0.3% |
| dodecylphenol polyethylene glycol ether | 0.5% |
| disodium phosphate | 1.0% |
| monosodium phosphate | 0.5% |
| Polyvinyl alcohol | 1.0% |
| water | 56.7% |

The ingredients are blended and ground together in a sand mill to produce particles essentially all under 5 microns in size.

EXAMPLE 10

Solution

| | |
|---|---|
| 2-[[N—(4-methoxy-6-methyl-1,3,5-triazin-2-yl)-N—methylaminocarbonyl]aminosulfonyl]benzcic acid, methyl ester | 5% |
| sodium salt | 5% |
| water | 95% |

The salt is added directly to the water with stirring to produce the solution, which may then be packaged for use.

EXAMPLE 11

Low Strength Granule

| | |
|---|---|
| 2-[[N—(4-methoxy-6-methyl-1,3,5-triazin-2-yl)-N—methylaminocarbonyl]aminosulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

Granule

| | |
|---|---|
| 2-[[N—(4-methoxy-6-methyl-1,3,5-triazin-2-yl)-N—methylaminocarbonyl]aminosulfonyl]benzoic acid, methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 13

High Strength Concentrate

| | |
|---|---|
| 2-[[N—(4-methoxy-6-methyl-1,3,5-triazin-2-yl)-N—methylaminocarbonyl]aminosulfonyl]benzoic acid, methyl ester | 99.0% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 14

Wettable Powder

| | |
|---|---|
| 2-[[N—(4-methoxy-6-methyl-1,3,5-triazin-2-yl)-N—methylaminocarbonyl]aminosulfonyl]benzoic acid, methyl ester | 90.0% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 15

Wettable Powder

| | |
|---|---|
| 2-[[N—(4-methoxy-6-methyl-1,3,5-triazin-2-yl)-N—methylaminocarbonyl]aminosulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 16

Oil Suspension

| | |
|---|---|
| 2-[[N—(4-methoxy-6-methyl-1,3,5-triazin-2-yl)-N—methylaminocarbonyl]aminosulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 17

Dust

| | |
|---|---|
| 2-[[N—(4-methoxy-6-methyl-1,3,5-triazin-2-yl)-N—methylaminocarbonyl]aminosulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

The compound of the instant invention may be used in combination with the following herbicides.

| | |
|---|---|
| 2,4-D | flurochloridone |
| 2,4-DB | fluroxypyr |
| barban | glyphosate |
| basagran | imazaquin |
| bentazone | ioxynil |
| benzoylpropethyl | isoproturon |
| bifenox | L-flampropisopropyl |
| bromofenoxium | linuron |
| bromoxynil | Lontrel |
| butraline | MCP |
| chlometexynil | MCPA |
| chlorfenprop-methyl | MCPB |
| clepyralid (3,6-DCP) | mecoprop (MCPP) |
| chlorsulfuron | methabenzthiazuron |
| chlortoluron | metoxuron |
| cyanazine | metribuzin |
| diallate | |
| dicamba | metsulfuron methyl |
| dichlorprop (2,4-DP) | neburon |
| diclofop-methyl | nitrofene |
| difenzoquat | paraquat |
| dinoseb (DNBP) | pendimethaline |
| dinoterbe | picloram |
| diquat | propanil |
| diuron | TBA |
| DNOC | terbutryn |
| flamprop isopropyl | triallate |
| flamprop methyl | trifluraline |

3-methyl-6-[4,5-dihydro-5-methyl-5-(1-methylethyl)-4-oxo-1H-imidazol-2-yl]benzoic acid, methyl ester 3-[[(4-methoxy-6-methyl-1,3,5-triazin-2-yl)aminocarbonyl]aminosulfonyl]-2-thiophenecarboxylic acid, methyl ester 4-chloro-2-[[(4-methoxy-6-methyl-1,3,5-triazin-2-yl)aminocarbonyl]aminosulfonyl]benzoic acid, (1-methyl ethyl)ester Most preferably in combination with:

3-[[(4-methoxy-6-methyl-1,3,5-triazin-2-yl)aminocarbonyl]aminosulfonyl]-2-thiophenecarboxylic acid, methyl ester;

3-methyl-6-[4,5-dihydro-5-methyl-5-(1-methylethyl)-4-oxo-1H-imidazol-2-yl]benzoic acid, methyl ester;

difenzoquat; or diclofop-methyl.

Utility

The compound of this invention is useful for the post-emergence control of weeds in the cereal crops wheat and barley. It controls a broad spectrum of broadleaf weeds with outstanding crop safety. Since it is rapidly dissipated in soil, it may be used in double cropping situations or where crops sensitive to herbicides now used in cereal crops will follow the cereal.

The rates of application are from 8 to 125 g/ha. The exact rate used will depend on the weeds to be controlled, and their stage of growth, the crop, the climate, other herbicides used in combination with it, formulation, etc. The exact rate to be used may be selected by one with ordinary skill in the art.

This compound may be used with other compounds selective on cereal crops including other sulfonylureas, the diarylethers, the ureas, the triazines and the carbamates.

The herbicidal properties of this chemical are shown in the greenhouse test that follows.

Procedure

Plastic trays were lined with polyethylene liners and filled with pasteurized Sassafras sandy loam soil (pH 6.5, 1% O.M.). One tray was planted with wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium* multiflorum), and rapeseed (*Brassica napus*). A second tray was planted with *Matricaria inodora*, cleavers bedstraw (*Galium aparine*), Russian thistle (*Salsola kali*), shepherdspurse (*Capsella bursa-pastoris*), kochia (*Kochia scoparia*), black nightshade (*Solanum nigrum*), speedwell (*Veronica persica*), wild buckwheat (*Polygonum convolvulus*), and sugarbeet (*Beta vulgaris*). For postemergence treatments, the first tray was planted 14 days before spraying, and the second tray was planted 24 days before treatment. Plants in the postemergence treatments ranged in height from 1 to 15 cm depending on specie. Wheat, barley, and wild oats were in the 2-leaf stage of development (Zadoks Stage 11). A second set of trays were prepared in an identical manner before spraying to service as preemergence treatments. Herbicides were diluted in a non-phytotoxic solvent and applied to the trays using a belt sprayer.

Additionally, three other species were evaluated: *Veronica hederaefolia*, chickweed (*Stellaria media*) and *Viola arvensis*. These plantings were grown in five inch pots containing the same soil as described previously. The plants were grown for 22 days before treatment. Herbicide application was made in a similar manner as the screening trays.

Plants were grown in the greenhouse for 21 days at which time visual ratings were made by comparing to an untreated control treatment. Ratings were based on a scale of 0=no effect to 100=complete kill.

TABLE II

| Rate (g/ha) | 125 | 64 | 32 | 16 | 8 | 4 | 2 |
|---|---|---|---|---|---|---|---|
| Preemergence | | | | | | | |
| Wheat | 0 | 0 | 0 | 0 | 0 | 0 | 0 |
| Barley | 0 | 0 | 0 | 0 | 0 | 0 | 0 |
| Sugarbeets | 100 | 100 | 80 | 80 | 60 | 50 | 20 |
| Rapeseed | 90 | 80 | 60 | 40 | 20 | 0 | 0 |
| Wild Oats | 0 | 0 | 0 | 0 | 0 | 0 | 0 |
| Cheatgrass | 0 | 0 | 0 | 0 | 0 | 0 | 0 |
| Blackgrass | 30 | 0 | 0 | 0 | 0 | 0 | 0 |
| Annual Bluegrass | 20 | 0 | 0 | 0 | 0 | 0 | 0 |
| Green Foxtail | 0 | 0 | 0 | 0 | 0 | 0 | 0 |
| Italian Ryegrass | 0 | 0 | 0 | 0 | 0 | 0 | 0 |
| *Matricaria inodora* | 50 | 40 | 20 | 0 | 0 | 0 | 0 |
| *Galium aparine* | 20 | 0 | 0 | 0 | 0 | 0 | 0 |
| Russian Thistle | 90 | 80 | 80 | 30 | 0 | 0 | 0 |
| Shepherdspurse | 90 | 80 | 70 | 70 | 30 | 20 | 0 |
| Kochia | 80 | 70 | 40 | 20 | 0 | 0 | 0 |
| Black Nightshade | 80 | 70 | 30 | 20 | 0 | 0 | 0 |
| Speedwell | 90 | 60 | 40 | 40 | 0 | 0 | 0 |
| Wild Buckwheat | 70 | 60 | 20 | 0 | 0 | 0 | 0 |
| Postemergence | | | | | | | |
| Wheat | 0 | 0 | 0 | 0 | 0 | 0 | 0 |
| Barley | 0 | 0 | 0 | 0 | 0 | 0 | 0 |
| Sugarbeets | 100 | 100 | 100 | 100 | 100 | 100 | 90 |
| Rapeseed | 100 | 100 | 100 | 100 | 100 | 90 | 80 |
| Wild Oats | 0 | 0 | 0 | 0 | 0 | 0 | 0 |
| Cheatgrass | 0 | 0 | 0 | 0 | 0 | 0 | 0 |
| Blackgrass | 40 | 20 | 0 | 0 | 0 | 0 | 0 |
| Annual Bluegrass | 30 | 20 | 0 | 0 | 0 | 0 | 0 |
| Green Foxtail | 70 | 40 | 0 | 0 | 0 | 0 | 0 |
| Italian Ryegrass | 0 | 0 | 0 | 0 | 0 | 0 | 0 |
| *Matricaria inodora* | 100 | 100 | 100 | 90 | 80 | 60 | 50 |
| *Galium aparine* | 70 | 50 | 30 | 20 | 0 | 0 | 0 |
| Russian Thistle | 100 | 100 | 100 | 100 | 90 | 90 | 70 |
| Shepherdspurse | 100 | 100 | 100 | 100 | 90 | 90 | 80 |
| Kochia | 100 | 100 | 100 | 100 | 80 | 70 | 50 |
| Black Nightshade | 90 | 80 | 80 | 70 | 60 | 60 | 50 |
| Speedwell | 100 | 90 | 80 | 70 | 50 | 30 | 30 |
| Wild Buckwheat | 90 | 90 | 80 | 70 | 70 | 30 | 0 |
| *Veronica hederaefolia* | 0 | 0 | 0 | 30 | 0 | 0 | 0 |
| *Viola arvensis* | 95 | 90 | 90 | 85 | 65 | 50 | 0 |
| *Stellaria media* | 100 | 100 | 100 | 95 | 95 | 80 | 75 |

What is claimed is:

1. A compound of the formula

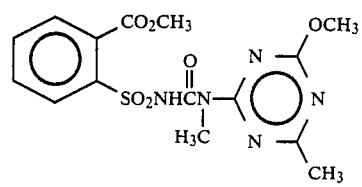

the compound which is 2-[[N-(4-methoxy-6-methyl-1,3,5-triazin-2-yl)-N-methylaminocarbonyl-]aminosulfonyl]benzoic acid, methyl ester.

2. A composition suitable for controlling the growth of undesired vegetation which comprises an effective amount of the compound of claim 1 and at least one of the following: surfactant, solid or liquid diluent.

3. A method for controlling the growth of undesired vegetation which comprises applying to the locus to be protected an effective amount of a compound of claim 1.

4. A composition suitable for controlling the growth of undesired vegetation in wheat and barley which comprises an effective amount of the compound of claim 1 and at least one of the following: surfactant, solid or liquid diluent.

5. A method for controlling the growth of undesired vegetation in wheat and barley which comprises applying to the locus to be protected an effective amount of a compound of claim 1.

6. A mixture of an effective amount of the compound of claim 1 with an effective amount of 3-[[(4-methoxy-6-methyl-1,3,5-triazin-2-yl)aminocarbonyl]-aminosulfonyl]-2-thiophenecarboxylic acid, methyl ester.

7. A method for controlling the growth of undesired vegetation which comprises applying to the locus to be protected an effective amount of the mixture of claim 6.

8. A method for controlling the postemergence growth of undesired vegetation in wheat or barley which comprises applying to the locus to be protected an effective amount of the compound of claim 1.

* * * * *